United States Patent [19]

Tieke et al.

[11] Patent Number: 4,756,848
[45] Date of Patent: Jul. 12, 1988

[54] CURABLE MIXTURES CONTAINING COPOLYMERIZABLE DIBENZALACETONE PALLADIUM COMPLEXES

[75] Inventors: Bernd Tieke, Giffers; Sheik A. Zahir, Oberwil, both of Switzerland; Jürgen Finter, Freiburg/Br., Fed. Rep. of Germany

[73] Assignee: Ciba-Geigy Corporation, Ardsley, N.Y.

[21] Appl. No.: 826,469

[22] Filed: Feb. 5, 1986

[30] Foreign Application Priority Data

Feb. 5, 1985 [CH] Switzerland .................. 514/85

[51] Int. Cl.⁴ .............................................. H01B 1/06
[52] U.S. Cl. ..................................... 252/511; 252/512; 252/514; 252/518; 252/506; 523/457; 523/459; 523/468; 525/524; 525/529
[58] Field of Search ............... 252/511, 512, 514, 518, 252/506; 523/457, 468; 525/524, 529; 556/136

[56] References Cited

U.S. PATENT DOCUMENTS 3,993,807 11/1976 Stabenow et al. ................. 427/229
4,347,232 8/1982 Michaelson ......................... 423/584

OTHER PUBLICATIONS

Chem. Abst. 84, 112305u (1976).
Chem. Abst. 90, 121805h (1979) and corresponding Derwent Abstract 00840B/01.
Y. Takahashi et al., J. Chem. Soc. D, 1970, 1065.

Primary Examiner—Josephine Barr
Attorney, Agent, or Firm—Edward McC. Roberts; Luther A. R. Hall

[57] ABSTRACT

Compounds of formula I

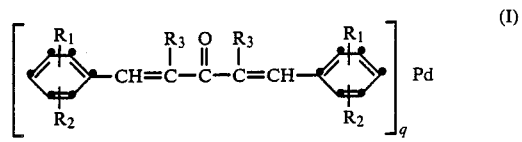

wherein $R_1$ is hydroxyl or glycidyloxy, $R_2$ is hydrogen, alkyl, alkoxy, halogen, aryl, aralkyl or alkaryl, $R_3$ is hydrogen or alkyl or both $R_3$s together are alkylene, and q is 1 to 3.5, together with epoxy resins and thermoactivatable hardeners and/or curing catalysts, are suitable for the preparation of curable mixtures. The cured products obtained therefrom can be employed for the preparation of electrically conductive coatings or patterns by tempering at elevated temperature or by irradiation with actinic light. Metal can be deposited without current on said electrically conductive coatings or patterns.

14 Claims, No Drawings

CURABLE MIXTURES CONTAINING COPOLYMERIZABLE DIBENZALACETONE PALLADIUM COMPLEXES

The invention relates to novel copolymerisable dibenzalacetone palladium complexes, to the preparation thereof, to mixtures containing palladium complexes of this invention, an epoxy resin and a hardener and/or curing catalyst, as well as to the use of said mixtures, e.g. as adhesives or for the preparation of cured products and in particular for the preparation of electroconductive coatings and patterns.

Palladium dibenzalacetone complexes were first described in 1970 by Takahashi et al. (J. Chem. Soc. D 1970, 1065). Such complexes may be employed as hydrogenation catalysts, or for the preparation of $H_2O_2$ or as catalysts for olefin/acetylene polymerisation (q.v. e.g. German Offenlegungsschrift No. 24 26 879, U.S. Pat. No. 4,347,232 and Japanese published patent application No. 53 132 527). Furthermore, it is known from German Offenlegungsschrift No. 24 51 217 that solutions of complexes of palladium, triphenyl phosphite and an olefinically or acetylenically unsaturated organic compound containing 3 to 16 carbon atoms or of palladium dibenzalacetone complexes may be employed for metal deposition without current on substrates such as metals, oxidised metals and plastics. The substrates to be coated are immersed one or more times in a solution of the palladium complexes, preferably in benzene or toluene solutions, and heated to 100°-300° C., with palladium being deposited on the substrate surface. The substrates so coated are suitable for metal deposition without current.

Metal deposition without current on epoxy resins with palladium as catalyst is likewise known. In said process the surface of the epoxy resin has to be activated with metallic Pd(O). Pd(O) can be produced e.g. chemically by the addition of reducing agents, such as $NaBH_4$, with formalin solution or thermally by heating to high temperatures.

Known activating baths contain for example $(NH_4)_2PdCl_4$, $(NH_4)_2Pd(NO_3)_4$, $PdCl_2$, $PdCl_2/NH_4CL$ or palladium organyls and polymers (q.v. e.g. Japanese published patent application No. 50 66 439 and German Offenlegungsschrift Specifications Nos. 21 16 389, 31 46 164 and 31 50 985). Finally, palladium-containing epoxy resins have also been described. The palladium may be present in colloidal form, in powder form, in the form of salts (Pd acetate, Pd bisacetylacrylate) or complexes (Pd allyl chloride) or in the form of an adduct of hexamethylenetetramine with palladium; however, in the case of said adduct, heating to 100° C. causes Pd(O) to be liberated [q.v. e.g. Japanese published patent applications Nos. 52 133 385 and 58 100 668, Tr. Mosk. Khim. Tekhnol. Inst. in D. I. Mendeleeva, 95 (1977) 124 and Japanese published patent application No. 49 128 832].

The present invention relates to novel copolymerisable compounds of formula I

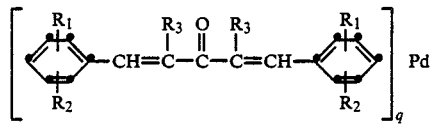
(I)

wherein $R_1$ is —OH or

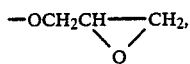

$R_2$ is a hydrogen atom, $C_1$-$C_4$ alkyl, $C_1$-$C_4$ alkoxy, halogen, $C_6$-$C_{10}$ aryl, $C_7$-$C_8$ aralkyl or $C_7$-$C_8$ alkaryl, $R_3$ is a hydrogen atom or $C_1$-$C_4$ alkyl or both substituents $R_3$ together form a polymethylene chain containing 2 to 4 carbon atoms and q is in the range from 1 to 3.5.

The compounds of formula I may also be present in the form of mixtures, in which case each symbol q may have a different meaning. q is preferably in the range from 2 to 3.5.

Alkyl or Alkoxy groups $R_2$ and $R_3$ may be straight chain or branched, e.g.: methyl, ethyl, n-propyl, isopropyl, n-butyl and sec-butyl; methoxy, ethoxy, n-propoxy, n-butoxy and sec-butoxy. Halogen atoms $R_2$ are preferably bromine and chlorine atoms. $R_2$ as aryl is for example 1- or 2-naphthyl and, preferably, phenyl. Examples of aralkyl or alkaryl groups $R_2$ in accordance with the definition are benzyl, $\alpha$- and $\beta$-phenylethyl, methylbenzyl, tolyl, xylyl and ethylphenyl.

Each of $R_2$ and $R_3$ is preferably a hydrogen atom.

$R_1$ is preferably attached in the m,m'-position and most preferably in the p,p'-position, with the preferred meaning of $R_1$ being

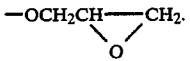

Particularly preferred compounds of formula I are those wherein $R_1$ is

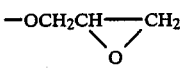

and each of $R_2$ and $R_3$ is a hydrogen atom.

The compounds of formula I can be prepared by methods which are known per se (q.v. e.g. J. Chem. Soc. D 1970, 1065 and U.S. Pat. No. 4,347,232) by reacting q moles of a compound of formula II

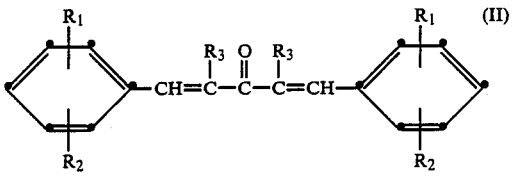
(II)

with a soluble palladium salt, in the presence of a base and, optionally, of a hydrogen donor. $R_1$, $R_2$, $R_3$ and q are as defined for formula I.

Examples of suitable bases are the alkali metal salts of aliphatic monocarboxylic acids, in particular potassium acetate and sodium acetate. Examples of suitable palladium salts are $PdBr_2$, $PdCl_2$ and $Na_2PdCl_4$, with $Na_2PdCl_4$ being particularly preferred and $PdCl_2$ being most preferred. The reaction is conveniently carried out in an organic solvent which simultaneously acts as hydrogen donor. Examples of suitable solvents are alkanols containing up to 6 carbon atoms, with ethanol being preferred and methanol being most preferred.

The compounds of formula II are known or can be prepared in a manner known per se, e.g. by a method analagous to that described in U.S. Pat. No. 3,295,974.

The present invention also relates to curable mixtures containing
(a) at least one compound of formula I,
(b) an epoxy resin or a mixture of epoxy resins and
(c) a thermoactivatable hardener and/or a curing catalyst.

Suitable epoxy resins (b) are preferably those containing on average more than one group of formula III

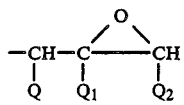
(III)

wherein each of Q and $Q_2$ is a hydrogen atom and $Q_1$ is a hydrogen atom or a methyl group or Q and $Q_2$ together are —CH$_2$CH$_2$—or —CH$_2$—CH$_2$—CH$_2$ and $Q_1$ is a hydrogen atom, which group is attached to a hetero atom, e.g. a sulfur atom and, preferably, to an oxygen or nitrogen atom.

Typical examples of such resins are polyglycidyl esters and poly($\beta$-methylglycidyl) esters which are derived from aliphatic, cycloaliphatic or aromatic polycarboxylic acids. Examples of suitable polycarboxylic acids are: succinic acid, glutaric acid, adipic acid, pimelic acid, suberic acid, azelaic acid, sebacic acid, dimerised or trimerised linoleic acid, tetrahydrophthalic acid, 4-methyltetrahydrophthalic acid, hexahydrophthalic acid, 4-methylhexahydrophthalic acid, phthalic acid, isophthalic acid and terephthalic acid.

Further examples are polyglycidyl ethers and poly($\beta$-methylglycidyl) ethers which are obtained by reacting a compound containing at least two alcoholic and/or phenolic hydroxyl groups per molecule with epichlorohydrin or with allyl chloride, and then epoxidising the reaction product with a peracid.

Examples of suitable polyols are: ethylene glycol, diethylene glycol, poly(oxyethylene) glycols, propane-1,2-diol, poly(oxypropylene) glycols, propane-1,3-diol, butane-1,4-diol, poly(oxytetramethylene) glycols, pentane-1,5-diol, hexane-2,4,6-triol, glycerol, 1,1,1-trimethylolpropane, pentaerythritol and sorbitol; resorcitol, quinitol, bis(4-hydroxycyclohexyl)methane, 2,2-bis(4-hydroxycyclohexyl) propane and 1,1-bis(hydroxymethyl)cyclohex-3-ene; N,N-bis(2-hydroxyethyl) aniline and 4,4'-bis(2-hydroxyethylamino)diphenylmethane; resorcinol, hydroquinone, bis(4-hydroxyphenyl)methane (bisphenol F), 2,2-bis(4-hydroxyphenyl)propane (bisphenol A), 2,2-bis(4-hydroxy-3,5-dibromophenyl)propane (tetrabromobisphenol A), 1,1,2,2-tetrakis(4-hydroxyphenyl)ethane, 4,4'-dihydroxybiphenyl, bis(4-hydroxyphenyl) sulfone, as well as novolaks of formaldehyde or acetaldehyde and phenol, chlorophenol or alkylphenols containing up to 9 carbon atoms in the alkyl moiety, preferably cresol and phenol novolaks.

Suitable poly(N-glycidyl) compounds are products obtained by dehydrochlorination of reaction products of epichlorohydrin and amines containing at least two active hydrogen atoms bonded to amino nitrogen atoms. Examples of suitable amines are: aniline, n-butylamine, bis(4-aminophenyl)methane, 1,3- and 1,4-xylylenediamine, 1,3and 1,4-bis(aminomethyl) cyclohexane and bis(4-methylaminophenyl) methane. Further suitable compounds are: triglycidyl isocyanurate, N,N'-diglycidyl derivatives of cyclic alkylene ureas such as ethylene urea and 1,3-propylene urea, or hydantoins such as 5,5-dimethylhydantoin.

Examples of poly(S-glycidyl) compounds are the di-S-glycidyl derivatives of dithiols such as ethanol1-1,2-dithiol and bis(4-mercaptomethylphenyl) ether.

Examples of epoxy resins containing one or more groups of the formula III, wherein Q and $Q_2$ together are a —CH$_2$CH$_2$— or —CH$_2$CH$_2$CH$_2$— group are bis(2,3-epoxycyclopentyl) ether, 2,3-epoxycyclopentyl glycidyl ether, 1,2-bis(2,3-epoxycyclopentyloxy)ethane, 3,4-epoxy-6-methylcyclohexylmethyl-3', 4'-epoxy-6'-methylcyclohexane carboxylate and 2-(3,4-epoxy)cyclohexyl-5,5-spiro(3',4'-epoxy) cyclohexane dioxane.

Also eligible are epoxy resins in which the epoxy groups are attached to hetero atoms of different kind, or in which some or all of the epoxy groups are central, for example the N,N,O-triglycidyl derivative of 4-aminophenol, N-glycidyl-N'-(2-glycidyloxypropyl)-5,5-dimethylhydantoin, vinylcyclohexane dioxide, limonene dioxide and dicyclopentadiene dioxide.

As component (b) it is particularly preferred to use diglycidyl ethers or advanced diglycidyl ethers of dihydric phenols in particular diglycidyl ethers or advanced diglycidyl ethers of 2,2-bis(4-hydroxyphenyl) propane, 2,2-bis(3,5-dibromo-4-hydroxyphenyl)propane, bis(4-hydroxyphenyl)methane, bis(4-hydroxycyclohexyl)methane or 2,2-bis(4-hydroxycyclohexyl) propane; polyglycidyl ethers of novolaks, or tetraglycidylated 4,4'-diaminodiphenylmethane. Most preferred are diglycidyl ethers or advanced diglycidyl ethers of bisphenol A, tetrabromo-bisphenol A or Bisphenol F, polyglycidyl ethers of phenol/formaldehyde or cresol/formaldehyde novolaks, or mixtures thereof.

If $R_1$ in formula I is —OH, then suitable hardeners (c) are e.g. aromatic and, in particular, aliphatic aldehydes containing 1 to 6 carbon atoms, polyisocyanates and polyepoxides.

Examples of suitable polyisocyanates are compounds of formula IV

(IV)

wherein X is —C$_p$H$_{2p}$—, where p is 1 to 8, cyclohexylene, phenylene, or tolylene, e.g. m- and p-phenylene diisocyanate, 1,6-hexamethylene diisocyanate and 2,4- or 2,6-tolylene diisocyanate.

If polyepoxides are employed as hardeners (c), then compounds of the type indicated under (b) are suitable. In this case, components (b) and (c) may therefore be identical.

Preferred hardeners (c) for OH group-containing compounds of formula I are formaldehyde or paraformaldehyde and, in particular, polyepoxides. As regards preferred epoxy resins when employing such hardeners, what has been stated above applies.

Suitable hardeners for compounds of formula I wherein $R_1$ is

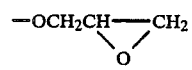

are in general any epoxy resin hardeners such as cyanamide, dicyanodiamide, polycarboxylic acids, polycarboxylic acid anhydrides, polyamines, polyiminoamides, adducts of amines and polyepoxides and polyols.

Suitable polycarboxylic acids and their anhydrides are e.g. phthalic anhydride, tetrahydrophthalic anhydride, hexahydrophthalic anhydride, methyltetrahydrophthalic anhydride, methyleneendomethylenetetrahydrophthalic anhydride, endomethylenetetrahydrophthalic anhydride, hexachloroendomethylenetetrahydrophthalic anhydride, trimellitic anhydride, pyromellitic anhydride, maleic anhydride, succinic anhydride, nonenylsuccinic anhydride, dodecenylsuccinic anhydride, polysebacic polyanhydride and polyazelaic polyanhydride as well as the acids pertaining to said anhydrides.

Examples of polyamines which are suitable hardeners are aliphatic, cycloaliphatic, aromatic and heterocyclic polyamines such as ethylenediamine, propane-1,2-diamine, propane-1,3-diamine, N,N-diethylethylenediamine, hexamethylenediamine, diethylenetriamine, triethylenetetramine, tetraethylenepentamine, N-(2-hydroxyethyl)-, N-(2-hydroxypropyl)- and N-(2-cyanoethyl)diethylenetriamine, 2,2,4-and 2,2,4-trimethylhexane-1,6-diamine, m-xylylenediamine, N,N-dimethyl- and N,N-diethylpropane-1,3-diamine, bis(94-aminocyclohexyl) methane, 2,2-bis(4-aminocyclohexyl)propane, 2,2-bis(4-amino-3-methylcyclohexyl) propane, 3-aminomethyl-3,5,5-trimethylcyclohexylamine (isophoronediamine), m- and p-phenylenediamine, bis(4-aminophenyl) methane, bis(4-aminophenyl)(sulfone, aniline-formaldehyde resins and N-2(2-aminoethyl)piperazine. Suitable polyaminoamides are e.g. those which are prepared from aliphatic polyamines and dimerised or trimerised unsaturated fatty acids.

Suitable adducts or amines with polyepoxides are e.g. adducts of aliphatic or cycloaliphatic diamines such as 1,6-hexamethylenediamine, 2,2,4- and 2,2,4-trimethylhexane-1,6-diamine or isophoronediamine with the above-mentioned diglycidyl ethers.

Suitable polyol hardeners (c) are in particular mono- or polynuclear aromatic polyols, including novolaks, such as resorcinol, hydroquinone, 2,6-dihydroxytoluene, pyrogallol, 1,1,3-tris(hydroxyphenyl)-propane, bis(4-hydroxyphenyl)methane, 2,2-bis(4-hydroxyphenyl)propane, bis(4-hydroxyphenyl)sulfone and 4,4'-dihydroxybiphenyl as well as novolaks of formaldehyde or acetaldehyde and phenol, chlorophenol or alkylphenols containing up to 9 carbon atoms in the alkyl moiety, in particular cresol and phenol novolaks.

Preferred hardeners for compounds of formula I containing glycidyloxy groups are polycarboxylic acid anhydrides such as tetrahydrophthalic anhydride, hexahydrophthalic anhydride and methyltetrahydrophthalic anhydride, as well as aromatic polyamines, in particular bis(4-aminophenyl)methane, bis(4-aminophenyl)sulfone and m- or p-phenylenediamine.

The hardeners (c) are employed in the amounts conventionally used in the art of epoxy resins, and conveniently in such amounts that about 0.7 to 1.5 equivalents of functional groups of the hardener (c) are present per one equivalent of OH and/or glycidyloxy groups.

Compounds which are known per se may also be employed as curing catalysts (c), e.g.: complexes of amines, in particular tertiary amines such as monoethylamine, trimethylamine and octyldimethylamine, with boron trifluoride or boron trichloride, monoesters of aspartic acid, e.g. 4-methyl-N-(3-dimethylaminepropyl)aspartate, and, in particular, unsubstituted or substituted imidazoles such as imidazole, benzimidazole, 1-methylimidazole, 2-ethyl-4-methylimidazole, 2-vinylimidazole, 2-phenylimidazole, 2-phenyl-4-methylimidazole, 1-(2,6-dichlorobenzoyl)-2-phenylimidazole and 1-(2,4,6-trimethylbenzoyl)-2-phenylimidazole. Imidazoles are preferred curing catalysts (c), with 2-phenylimidazole and 2-ethyl-4-methylimidazole being most preferred.

The mixtures of this invention may also contain as further component (d) curing accelerators. Suitable accelerators are e.g. tertiary amines such as benzyldimethylamine, tris(dimethylaminomethyl)phenol, hexamethylenetetramine or 1,6-bis(dimethylamino)hexane; aromatic carbonates, such as diphenyl carbonate and urea derivatives such as N-4-chlorophenyl-N',N-dimethylurea (nonuron), N-3-chloro-4-methylphenyl-N', N-dimethylurea (chlorotoluron) and N-(2-hydroxy-4-nitrophenyl)-N', N-dimethylurea. Tertiary amines are preferred curing accelerators (d), with benzyldimethylamine being most preferred.

The components (c) and (d) are employed in the customary effective amounts, i.e. in amounts sufficient for the curing of the mixtures of the invention. The ratio of the components (a), (b), (c) and, if present, (d) is dependent on the nature of the compounds employed, the required curing rate and the properties desired in the final product and can readily be determined by the person skilled in the art of epoxy resin curing. The amount of palladium complex of formula I can vary within wide limitsand is conveniently in the range from 0.01 to 60% by weight, preferably from 0.1 to 40% by weight, based on the total weight of the mixture.

In addition to further customary additives, the mixtures of the invention may also contain electrically conductive fillers (3), conveniently in amounts of 1 to 90% by weight, preferably 40 to 80% by weight, based on the total weight of the mixture, with the sum of components (a) to (e) being 100% by weight. Suitable electrically conductive fillers are those of organic or inorganic nature such as carbon black and graphite or metals of Periodic Groups Vb, VIb, VIII and Ib, alloys and salts thereof such as halides, oxides and sulfides.

Examples of suitable metals and metal compounds are: vanadium, niobium, tantalum, molybdenum, tungsten, copper, noble metals such as Pt, Pd, Ag and Au, AgPd alloys, silver oxide, silver iodide, copper(II) sulfide, copper (I) iodide, copper(II) oxide, gold(III) bromide, gold(III) iodide and gold(III) oxide, molybdenum(IV) sulfide, niobium(IV) chloride and niobium(IV) oxide, palladium iodide, palladium oxide, platinum(IV) bromide and platinum(IV) chloride, vanadium(III) chloride, vanadium(IV) oxide, tungsten(VI) chloride and tungsten(VI) oxide. Preferred metals are silver, copper, silver/palladium alloys, palladium, platinum, gold, tungsten and molybdenum. Particularly preferred metals are Au, Pt, AgPd, with Ag and Cu powder being most preferred.

The mixtures of the invention may also contain further known additives conventionally employed in the art of epoxy resins. Examples of such additives are: pigments, dyes, reinforcing materials such as glass fibres, flame retardants, reactive diluents for the epoxy resins, e.g. phenyl and cresyl glycidyl ethers, butanediol diglycidyl ethers and hexahydrophthalic acid diglycidyl ethers, antistatic agents, levelling agents, mould release agents, adhesion promoters, antioxidants and light stabilisers.

The compounds of formula I are readily soluble in epoxy resins and the resultant solutions have a relatively low viscosity.

The mixtures of the invention can be employed e.g. as adhesives or for the preparation of cured products, in particular of castings, laminates and thin coatings (films).

Curing of the mixtures of the invention is generally carried out by heating to temperatures in the range from 80° to 200° C., preferably from 100° to 180° C. Surprisingly, the compounds of formula I are incorporated in undestroyed form and finely dispersed into the network of the cured products without impairment of the mechanical properties of said cured products.

Thermal treatment of the cured products at elevated temperature (tempering) or irradiation with actinic light may result in finely dispersed elementary palladium [palladium(0)] being liberated which diffuses onto the surface of the resin and forms there an electrically conductive film. Accordingly, the invention also relates to the use of the mixtures of the invention for the preparation of electrically conductive coatings and patterns, in particular for printed circuits, which comprises, after curing, tempering the mixture at elevated temperature or irradiating said mixture with actinic light.

Tempering is preferably carried out at temperatures above 220° C., preferably in the temperature range from 220° to 250° C. Irradiation can be effected with visible light as well as with UV light having a wavelength of 200–600 nm. Suitable light sources are e.g. xenon lamps, argon lamps, tungsten lamps, carbon arcs, metal halide and metal arc lamps such as low pressure, medium-pressure and high-pressuree mercury lamps, argon ion lasers, frequency doubled Nd-YAG lasers (yttrium-/aluminium garnet) and UV lasers.

It is preferred to effect irradiation with visible light.

The electrically conductive coatings or patterns obtained after tempering or after irradiation with actinic light are particularly suitable for metal disposition without current, with electrically conductive metallic coatings or patterns being obtained. The metal deposition without current can be carried out with metallisation baths known per se and by conventional methods. Suitable metals are for example copper, nickel, cobalt, silver and tin or cobalt/phosphorous and cobalt/nickel alloys.

The invention is illustrated in more detail by the following Examples.

EXAMPLE 1

Preparation of tris (dibenzalacetone bis-p,p'-glycidyl ether) palladium

With vigorous stirring, 15 g of PdCl₂ are boiled in a solution of 10.7 g of NaCl in 65 ml of water until the palladium chloride is completely dissolved. The water is then distilled off. The residue is taken up in 200 ml of methanol and the solution is heated to 60° C. 105.9 g of dibenzalacetone bis-p,p'-diglycidyl ether and 42.8 g of sodium acetate. 3H₂O are added, followed by the addition of another 175 ml of methanol. After a further 15 minutes at 60° C., the mixture is cooled. A precipitate forms which is isolated by filtration under argon and washed with one ml portion of methanol, with three 100 ml portions of water and then with two more 100 ml portions of methanol. The product is subsequently dried in vacuo at 50° C. For the complete removal of the residual dibenzalacetone bis-p,p'-diglycidyl ether, the crystals are suspended in 700 ml of methanol and then isolated by filtration under argon. Subsequent drying in vacuo affords 100.7 g of violet crystals which are readily soluble in chloroform, methylene chloride, benzene, cyclohexane, acetone, ethyl acetate and cellosolve (2-ethoxyethanol). Further properties of the resultant complex are indicated in Table I.

EXAMPLE 2

Preparation of the p,p'-dihydroxydibenzalacetone palladium complex

The procedure described in Example 1 is repeated using 71 g of recrystallised p,p'-dihydroxydibenzalacetone in place of 105.9 g of dibenzalacetone bis-p,p'-diglycidyl ether. Dring working up the product is washed with two 30 ml portions of methanol and one 150 ml portion of ethyl acetate. 55.6% of violet crystals are obtained which are readily soluble in alcohols such as methanol and ethanol, in benzene, toluene, acetone and 2-ethoxyethanol. Further properties of the resultant complex are indicated in Table I.

TABLE I

| Palladium complex according to | Example 1 | Example 2 |
|---|---|---|
| $C_{found}$ (%) | 66.25 | 53.14 |
| $H_{found}$ (%) | 5.45 | 4.13 |
| $Pd_{found}$ (%) | 8.10 | 24.6 |
| q found | 3.2 | 1.1 |
| yield (%) | 97.4 | 55.6 |
| decomposition range (°C.) | 120–160 | 150–180 |
| decomposition maximum (°C.) | 140 | 173 |

EXAMPLE 3

With stirring, 25.7 g (34.8% by weight) of a bisphenol A diglycidyl ether with an epoxide content of 5.25–5.4 equivalents/kg, 18.6 g (25.1% by weight) of the palladium complex according to Example 1 and 29.4 g (39.8% by weight) of hexahydrophthalic anhydride are mixed in vacuo for 1 hour at 90° C. Then 0.22 g (0.3% by weight) of benzyldimethylamine as accelerator is added. After stirring for a further 5 minutes at 90° C., the mixture is poured into a mould which has been preheated to 100° C. The mixture is then cured for 4 hours at 100° C. and for 4 hours at 120° C. The properties of the moulded article obtained are indicated in Table II.

EXAMPLE 4

With stirring, 44.8 g (54.6% by weight) of the bisphenol A diglycidyl ether according to Example 3 and 20.7 g (25.2% by weight) of the palladium complex according to Example 1 are mixed in vacuo for 30 minutes at 90° C. Then 16.6 g (20.2% by weight) of 4,4'-diaminophenylmethane are added and the mixture is stirred in vacuo for a further 10 minutes at 90° C. The mixture is subsequently poured into a mould which has been preheated to 100° C. The mixture is then cured for 4 hours at 100° C., 4 hours at 120° C., 2 hours at 150° C. and 2 hours at 180° C. The properties of the moulded article obtained are indicated in Table II.

EXAMPLE 5

With stirring, 8.0 g (25.2% by weight) of the palladium complex according to Example 1 and 23.1 g (72.9% by weight) of the bisphenol A diglycidyl ether according to Example 3 are mixed in vacuo for 30 minutes at 90° C. Then 0.61 g (1.9% by weight) of 2-phenylimidazole as curing catalyst is added. After stirring in vacuo for a further 10 minutes at 90° C., the mixture is poured into a mould which has been preheated to 100° C. The mixture is then cured for 4 hours at 100° C. and for 4 hours at 120° C. The properties of the moulded article obtained are indicated in Table II.

EXAMPLE 6

Preparation of a Multilayer Epoxy Glass Fibre Laminate

Solutions of the following formulations are prepared:

(1)
- 6.3 g (25.0% by wt.) of the palladium complex according to Example 1
- 11.5 g (46.0% by wt.) of a solid epoxy resin based on bis-phenol A with an epoxide content of 2.15-2.22 equiv./kg
- 7.2 g (28.7% by wt.) of hexahydrophthalic anhydride
- 0.1 g (0.3% by wt.) of benzyldimethylamine, dissolved in 25 ml of dichloromethane (2)
- 100.0 g (77.9% by wt.) of a solid epoxy resin based on bisphenol A with an epoxide content of 2.15-2.22 equiv./kg
- 27.8 g (21.6% by wt.) of hexahydrophthalic anhydride
- 0.4 g (0.3% by wt.) of benzyldimethylamine, dissolved in 125 ml of dichloromethane (3)
- 3.7 g (14.8% by wt.) of the palladium complex according to Example 1
- 3.7 g (14.9% by wt.) of dibenzalacetone diglycidyl ether
- 14.3 g (57.0% by wt.) of a solid epoxy resin based on bisphenol A with an epoxide content of 2.15-2.22 equiv./kg
- 3.3 g (13.3% by wt.) of 4,4'-methylenedianiline (4)
- 90.6 g (90.6% by wt.) of a solid epoxy resin based on bisphenol A with an epoxide content of 2.15-2.22 equiv./kg
- 9.4 (9.4% by wt.) of 4,4'-methylenedianiline, dissolved in 100 ml of dichloromethane Prepegs are prepared by immersing glass fibre mats into each of the solutions (1), (2), (3) and (4) and subsequently evaporating off the solvent. 9 prepegs of solution (2) are coated with 1 prepeg of solution (1) and then moulded to a stable laminate by curing for 6 hours at 120° C. Likewise, 10 prepegs of solution (4) are coated with 2 prepegs of solution (3) and then moulded to a stable laminate by curing for 6 hours at 120° C.

EXAMPLE 7

Liberation of metallic palladium on the surface of casting resins and laminates

A sample of each of the casting resins prepared in accordance with Examples 3, 4 and 5 and a sample of the laminate prepared in accordance with Example 6 are air-tempered for 1 hour at $\geq 220°$ C. An electrically conductive palladium film is formed on the resin surface. (For conductivity values cf. Table II).

EXAMPLE 8

Selective liberation of metallic palladium on the surface of casting resins and laminates A sample of each of the casting resins prepared in accordance with Examples 3, 4 and 5 and a sample of the laminate prepared from solutions (1) and (2) in accordance with Example 6 are irradiated with a laser for 3 seconds ($\lambda = 514$ nm, 18 A, 0.35 W). A palladium film is deposited on the irradiated areas of the surface.

EXAMPLE 9

Metal deposition without current

The casting resins and laminates pretreated in accordance with Examples 7 and 8 are immersed in a commercially available deposition bath for copper- or nickel-plating without current.

(a) Copper-plating bath (A) SHIPLEY-Cuposit ®CP-8 or (B) SHIPLEY-Cuposit ® Copper Mix 328 Q. Bath composition according to "Printed Circuit Handbooks", 2 edition, C. F. Coombs, Jr. et al., McGraw Hill Book Co., New York, 1979, pp 7-5:
- 25 g/l of $CuSO_4.5H_2O$
- 60 g/l of sodium gluconate
- 20 g/l of NaOH
- 25 g/l of 37% aqueous formaldehyde solution, under a flow of oxygen.

Operating temperature: 20° C.

(b) Nickel-plating bath according to J. Appl. Electrochem., 1 (1971) 167:
- 30 g/l of $NiCl_2.6H_2O$
- 10 g/l of $NaH_2PO_2.H_2O$
- 50 g/l of $NH_4Cl$
- 82.4 g/l of sodium citrate.$2H_2O$.

The pH of the bath is adjusted with concentrated $NH_4OH$ to 9. Operating temperature: 90° C.

After 1.5 minutes a firmly adhering copper or nickel film is formed on the areas of the resin which have been thermally pretreated.

TABLE II

| | Properties of the moulded articles | | |
|---|---|---|---|
| | Moulded article according to Example | | |
| | 3 | 4 | 5 |
| dielectric dissipation factor tan δ [× 10²] | 0.89 (23° C.) | 0.48 (26.4° C.) | 0.48 (26.7° C.) |
| dielectric constant ε ($T_1$) | 3.5 (23° C.) | 4.9 (26.4° C.) | 4.5 (26.7° C.) |
| dielectric constant ε ($T_2$) | 3.5 (100° C.) | 4.7 (100.5° C.) | 4.6 (100.4° C.) |
| specific volume resistance ρ [Ω cm] | $3.6 \times 10^{16}$ (23° C.) | $2.5 \times 10^{15}$ (27° C.) | $1.9 \times 10^{15}$ (26.4° C.) |
| | $1.6 \times 10^{15}$ (100° C.) | $7.3 \times 10^{14}$ (98.8° C.) | $4.3 \times 10^{12}$ (100.4° C.) |
| flexural strength acc. to DIN 53 435 (N/mm²) | 152.5 | 135.9 | n.d. |
| bending angle [°] | 57.1 | 55.7 | n.d. |
| ultimate strength acc. to DIN 53 435 [KJm⁻²] | 7.1 | 12.7 | n.d. |
| water absorption | | | |
| after 1 hour at 100° C. (%) | 0.31 | 0.51 | n.d. |
| after 4 days at 20° C. (%) | 0.33 | 0.50 | n.d. |
| thermal conductivity acc. to DIN 52612 [W/(K·m)] | 0.250 | 0.291 | n.d. |
| surface conductivity after | $\geq 10^1$ | $\geq 10^1$ | $\geq 10^1$ |

TABLE II-continued

| | Properties of the moulded articles | | |
| --- | --- | --- | --- |
| | Moulded article according to Example | | |
| | 3 | 4 | 5 |
| tempering for 2 hours at 220° C. [S cm$^{-1}$] | | | | n.d. = not determined

What is claimed is:

1. A curable mixture which comprises 0.01 to 60% by weight of
   (a) at least one compound of formula I

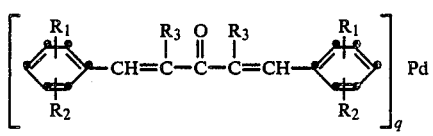

wherein
$R_1$ is —OH or

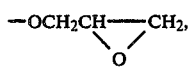

$R_2$ is a hydrogen atom, $C_1$-$C_4$alkyl, $C_1$-$C_4$alkoxy, halogen, $C_6$-$C_{10}$aryl, $C_7$-$C_8$aralkyl or $C_7$-$C_8$alkaryl, $R_3$ is a hydrogen atom or $C_1$-$C_4$alkyl or both substituents $R_3$ together form a polymethylene chain containing 2 to 4 carbon atoms and q is in the range from 1 to 3.5, (b) an epoxy resin or mixture of epoxy resins, and
(c) an effective amount of a thermoactivatable hardener, a curing catalyst or a mixture thereof.

2. A curable mixture according to claim 1, which additionally contains (e) 1 to 90% by weight of an electrically conductive filler.

3. A curable mixture according to claim 1, wherein the epoxy resin (b) is an epoxy resin containing on average more than one group of formula (III)

wherein each of Q and $Q_2$ is a hydrogen atom and $Q_1$ is a hydrogen atom or a methyl group or Q and $Q_2$ together are —CH$_2$—CH$_2$— or —CH$_2$—CH$_2$—CH$_2$— and $Q_1$ is a hydrogen atom, which group is attached to a sulfur, oxygen or nitrogen atom.

4. A curable mixture according to claim 1, wherein the epoxy resin (b) is a diglycidyl ether or an advanced diglycidyl ether of 2,2-bis(4-hydroxyphenyl)propane, 2,2-bis(3,5-dibromo-4-hydroxyphenyl) propane, bis(4-hydroxyphenyl)methane, bis(4-hydroxycyclohexyl) methane or 2,2-bis(4-hydroxycyclohexyl)propane, a polyglycidyl ether of a novolak, or tetraglycidylated 4,4'-diaminodiphenylmethane.

5. A curable mixture according to claim 1, wherein the epoxy resin (b) is a diglycidyl ether or an advanced diglycidyl ether of bisphenol A or bisphenol F, a polyglycidyl ether of a phenol/formaldehyde or cresol/formaldehyde novolak or a mixture of such resins.

6. A curable mixture according to claim 1, wherein if $R_1$=—OH, the hardener (c) is an aromatic aldehyde or an aliphatic aldehyde containing 1 to 6 carbon atoms, a polyisocyanate or polyepoxide.

7. A curable mixture according to claim 1, wherein if

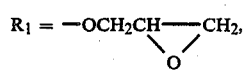

the hardener (c) is a polycarboxylic anhydride or an aromatic polyamine.

8. A curable mixture according to claim 1, wherein, if

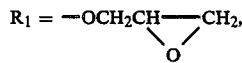

the curing catalyst (c) is an imidazole, preferably 2-phenylimidazole or 2-ethyl-4-methylimidazole.

9. A curable mixture according to claim 1, which additionally contains (d) a curing accelerator.

10. A curable mixture according to claim 9, wherein the accelerator is a tertiary amine.

11. A curable mixture according to claim 1, which contains 0.1 to 40% by weight of a compound of formula I, based on the total weight of the mixture.

12. A curable mixture according to claim 10 wherein the accelerator is benzyldimethylamine.

13. An adhesive or cured product which is a casting, laminate or film prepared using the mixture of claim 1.

14. A product according to claim 13 which contains 1 to 90% by weight of an electrically conductive filler.

* * * * *